(12) United States Patent
Yamashita et al.

(10) Patent No.: US 11,116,408 B2
(45) Date of Patent: Sep. 14, 2021

(54) BIOLOGICAL INFORMATION MEASUREMENT SUPPORT DEVICE, BIOLOGICAL INFORMATION MEASUREMENT DEVICE, AND BIOLOGICAL INFORMATION MEASUREMENT SUPPORT METHOD

(71) Applicant: OMRON HEALTHCARE CO., LTD., Kyoto (JP)

(72) Inventors: Shingo Yamashita, Muko (JP); Naoki Maeda, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 368 days.

(21) Appl. No.: 16/222,058

(22) Filed: Dec. 17, 2018

(65) Prior Publication Data

US 2019/0117082 A1    Apr. 25, 2019

Related U.S. Application Data

(63) Continuation of application No. PCT/JP2017/022718, filed on Jun. 20, 2017.

(30) Foreign Application Priority Data

Jun. 24, 2016  (JP) .............................. JP2016-125646

(51) Int. Cl.
  *G06F 1/3203*    (2019.01)
  *A61B 5/02*    (2006.01)
  (Continued)

(52) U.S. Cl.
  CPC ................ *A61B 5/02* (2013.01); *A61B 5/022* (2013.01); *A61B 5/746* (2013.01); *A61B 5/7445* (2013.01); *G06F 1/3212* (2013.01)

(58) Field of Classification Search
  CPC ......... A61B 5/02; A61B 5/022; A61B 5/7445; A61B 5/746; A61B 5/7221; A61B 5/02416; A61B 5/021
  (Continued)

(56) References Cited

U.S. PATENT DOCUMENTS

2005/0187480 A1* 8/2005 Kario ................. A61B 5/02422
                                                          600/483
2006/0020216 A1* 1/2006 Oishi ................... A61B 5/0205
                                                          600/500

(Continued)

FOREIGN PATENT DOCUMENTS

CN        102333481        1/2012
CN        104188663        12/2014

(Continued)

OTHER PUBLICATIONS

International Search Report dated Sep. 19, 2017 in International (PCT) Application No. PCT/JP2017/022718 with English translation.

(Continued)

*Primary Examiner* — Volvick Derose
(74) *Attorney, Agent, or Firm* — Wenderoth, Lind & Ponack, L.L.P.

(57) ABSTRACT

A system control unit in the biological information measurement device generates and reports measurement efficiency information indicating measurement efficiency for biological information included in biological information calculation results information, based on biological information calculation results information and pulse wave detection results information from a storage medium storing the biological information calculation results information and the pulse wave detection results information, said biological information calculation results information being information indicating the calculation results for biological infor- (Continued)

mation from a biological information calculation unit that calculates biological information based on pulse waves for each pulse detected for a living body, said biological information calculation results information including at least the biological information, and said pulse wave detection results information indicating results from pulse wave detection performed for calculating biological information included in the biological information calculation results information.

21 Claims, 13 Drawing Sheets

(51) Int. Cl.
*A61B 5/022* (2006.01)
*A61B 5/00* (2006.01)
*G06F 1/3212* (2019.01)

(58) Field of Classification Search
USPC .......................................................... 600/301
See application file for complete search history.

(56) References Cited

U.S. PATENT DOCUMENTS

| | | | |
|---|---|---|---|
| 2008/0208064 A1* | 8/2008 | Lee | A61B 5/024 600/485 |
| 2008/0242956 A1 | 10/2008 | Suzuki et al. | |
| 2010/0268098 A1* | 10/2010 | Ito | A61B 5/022 600/490 |
| 2011/0144918 A1* | 6/2011 | Inoue | A61B 5/02225 702/19 |
| 2011/0301476 A1 | 12/2011 | Sawanoi et al. | |
| 2012/0014233 A1 | 1/2012 | Lee et al. | |
| 2012/0015778 A1 | 1/2012 | Lee et al. | |
| 2012/0015779 A1 | 1/2012 | Powch et al. | |
| 2012/0173978 A1 | 7/2012 | Lee et al. | |
| 2012/0203119 A1* | 8/2012 | Yamashita | A61B 5/6824 600/490 |
| 2013/0023778 A1* | 1/2013 | Sawanoi | A61B 5/02255 600/499 |
| 2015/0282748 A1 | 10/2015 | Hamaguchi et al. | |
| 2015/0366473 A1* | 12/2015 | Shimuta | A61B 5/349 600/479 |
| 2016/0029908 A1* | 2/2016 | Usuda | A61B 5/02225 600/494 |
| 2016/0081630 A1* | 3/2016 | Aoshima | A61B 5/0205 600/301 |
| 2016/0135691 A1 | 5/2016 | Dripps et al. | |
| 2016/0358504 A1 | 12/2016 | Powch et al. | |
| 2017/0112448 A1 | 4/2017 | Liu et al. | |
| 2017/0281024 A1* | 10/2017 | Narasimhan | A61B 5/6824 |
| 2017/0340219 A1* | 11/2017 | Sullivan | A61B 5/6824 |
| 2020/0108305 A1 | 4/2020 | Lee et al. | |

FOREIGN PATENT DOCUMENTS

| | | | | |
|---|---|---|---|---|
| CN | 104361207 | | 2/2015 | |
| CN | 104706336 | | 6/2015 | |
| CN | 104812303 | | 7/2015 | |
| CN | 105263403 | | 1/2016 | |
| EP | 3 005 940 | | 4/2016 | |
| JP | 62-114533 | | 5/1987 | |
| JP | 2007-215722 | | 8/2007 | |
| JP | 2008-237574 | | 10/2008 | |
| JP | 2010-88576 | | 4/2010 | |
| JP | 2015-047400 | | 3/2015 | |
| JP | 2015047400 A | * | 3/2015 | ............ A61B 5/022 |
| JP | 2015-150023 | | 8/2015 | |
| WO | 2016/061239 | | 4/2016 | |

OTHER PUBLICATIONS

Written Opinion of the International Searching Authority dated Sep. 19, 2017 in International (PCT) Application No. PCT/JP2017/022718.
Extended European Search Report dated Dec. 19, 2019 in corresponding European Patent Application No. 17815405.0.
Office Action dated Feb. 3, 2021 in corresponding Chinese Patent Application No. 201780037849.8, with English translation.

* cited by examiner

FIG. 3

| PULSE WAVE DETECTION TIME PERIOD INFORMATION | DATE AND TIME OF PULSE WAVE DETECTION | PULSE WAVE INFORMATION | BIOLOGICAL INFORMATION | MEASUREMENT FLAG |
|---|---|---|---|---|
| **** | **** | **** | **** | 0 |
| | **** | **** | **** | 0 |
| | **** | **** | **** | 0 |
| | **** | **** | — | 1 |
| | **** | **** | — | 1 |
| | **** | **** | — | 1 |
| | **** | **** | **** | 0 |
| | **** | **** | **** | 0 |
| | **** | **** | **** | 0 |
| | **** | **** | **** | 0 |
| | ... | ... | ... | ... |

(a) MEASUREMENT SUCCESS RATE
80%

(b) NUMBER OF VALID DATA/
TOTAL NUMBER OF DATA
24,000/30,000

(c) MEASUREMENT FAILURE RATE
20%

(d) NUMBER OF INVALID DATA/
TOTAL NUMBER OF DATA
6,000/30,000

(a)

(b)

BIOLOGICAL INFORMATION MEASUREMENT SUPPORT DEVICE, BIOLOGICAL INFORMATION MEASUREMENT DEVICE, AND BIOLOGICAL INFORMATION MEASUREMENT SUPPORT METHOD

CROSS REFERENCE TO RELATED APPLICATIONS

This application is a continuation of PCT application No. PCT/JP2017/022718, which was filed on Jun. 20, 2017 based on Japanese Patent Application (No. P2016-125646) filed on Jun. 24, 2016, the contents of which are incorporated herein by reference.

BACKGROUND OF THE INVENTION

The present invention relates to a biological information measurement support device, a biological information measurement device, a biological information measurement support method, and a biological information measurement support program.

In general, the biological information necessary for in vivo diagnosis such as blood pressure information, pulse information, heartbeat information and the like largely changes in the day. For this reason, the biological information is continuously measured and recorded from a measurement subject for diagnosis and the like.

As a device configured to continuously measure the biological information, a device configured to detect a pulse wave every one pulse (a time period for which the heart beats one time) and to calculate and store the biological information in a unit of one pulse based on the detected pulse wave has been known. Also, a biological information measurement device configured to display an outline of the measured biological information or a reliability rate so as to inform a user of a measurement result and to support doctor's determination for taking a next action has been suggested (refer to Patent Documents 1 and 2).

Patent Document 1 discloses a biological information measurement device configured to continuously measure blood pressure information more than once by an oscillometric method and to display a reliability rate indicative of reliability of each of the measured blood pressure information after the multiple measurements of the blood pressure information are over. A doctor makes a diagnosis based on the other blood pressure information except the blood pressure information having a low reliability rate, based on the displayed reliability rates, thereby increasing the accuracy of the diagnosis.

Patent Document 2 discloses an activity meter having a heart rate measuring function and configured to display a trend graph of the heart rates at an end of measurement. A user of the activity meter can check activity situations of the user by seeing the trend graph and utilize the trend graph for exercise management, physical condition management and the like.

Patent Document 1: JP-A-2010-88576
Patent Document 2: JP-A-2007-215722

SUMMARY

A biological information measurement support device of the present invention includes a notification processing unit configured to execute processing of acquiring measurement efficiency information and notifying the measurement efficiency information, wherein the measurement efficiency information is generated by a measurement efficiency information generation unit configured to generate the measurement efficiency information based on biological information calculation result information and pulse wave detection result information which are stored in a storage medium, the biological information calculation result information is indicative of a calculation result of biological information made by a biological information calculation unit configured to calculate the biological information based on a pulse wave detected from a living body, the biological information calculation result information includes at least the biological information calculated based on the pulse wave, the pulse wave detection result information is indicative of a result of pulse wave detection processing executed to calculate the biological information to be included in the biological information calculation result information, and the measurement efficiency information is indicative of a measurement efficiency of the biological information to be included in the biological information calculation result information.

A biological information measurement device of the present invention includes a pulse wave detection unit configured to detect a pulse wave from a living body;

a biological information calculation unit configured to calculate biological information based on the pulse wave detected by the pulse wave detection unit and to store, as information indicative of a calculation result of the biological information, biological information calculation result information comprising at least the biological information in a storage medium;

a storage control unit configured to store, in the storage medium, pulse wave detection result information indicative of a result of pulse wave detection processing executed by the pulse wave detection unit to calculate the biological information to be included in the biological information calculation result information; and the biological information measurement support device.

A biological information measurement support method of the present invention includes a step of acquiring measurement efficiency information from a measurement efficiency information generation unit, the measurement efficiency information generation unit being configured to generate the measurement efficiency information based on biological information calculation result information and pulse wave detection result information of a storage medium in which, as information indicative of a calculation result of biological information made by a biological information calculation unit configured to calculate the biological information based on pulse waves detected from a living body, the biological information calculation result information including at least the biological information calculated based on the pulse waves and the pulse wave detection result information indicative of a result of pulse wave detection processing executed to calculate the biological information to be included in the biological information calculation result information are stored, the measurement efficiency information being indicative of a measurement efficiency of the biological information to be included in the biological information calculation result information, and a step of executing processing of notifying the measurement efficiency information.

A non-transitory computer-readable storage medium, which stores a biological information measurement support program of the present invention is configured to enable a computer to execute a step of acquiring measurement efficiency information from a measurement efficiency information generation unit, the measurement efficiency information generation unit being configured to generate the measurement efficiency information based on biological information calculation result information and pulse wave detection result information of a storage medium in which, as information indicative of a calculation result of biological information made by a biological information calculation unit configured to calculate the biological information based on pulse waves detected from a living body, the biological information calculation result information including at least the biological information calculated based on the pulse waves and the pulse wave detection result information indicative of a result of pulse wave detection processing executed to calculate the biological information to be included in the biological information calculation result information are stored, the measurement efficiency information being indicative of a measurement efficiency of the biological information to be included in the biological information calculation result information, and a step of executing processing of notifying the measurement efficiency information.

BRIEF DESCRIPTION OF THE DRAWINGS

FIG. 3 depicts an example of a data structure of measured data that is to be stored in a storage medium 13 of the biological information measurement device 1 shown in FIG. 1.

FIG. 8 depicts a screen example in which an image based on information generated by a fourth measurement efficiency information generation method is displayed on the display unit 15.

DETAILED DESCRIPTION OF THE EXEMPLARY EMBODIMENTS

The biological information measurement device configured to measure the biological information in a unit of one pulse is used with being worn on a body of the measurement subject for a long time. For this reason, when the body motion of the measurement subject largely changes, the pulse wave may deviate from a correct value.

A technology of detecting the body motion and correcting the biological information based on the detected body motion has been known. However, it is not easy to correct the biological information that is being measured while the body motion changes. Therefore, it is advantageous from the aspect of cost to treat the measurement of the biological information as failure or unmeasurable for a time period in which the body motion largely changes.

Thus, in the biological information measurement device that is assumed to be used with being worn on the living body for a long time, it is considered to determine a measurement success and a measurement failure of the biological information in the device and to store only a successfully measured measurement result.

However, the determination is made in the device, so that the measurement subject cannot know the same. For this reason, if the measurement subject wears the biological information measurement device, assumes that the biological information is always measured successfully and has a regular life, a time period in which the measurement of the biological information actually fails may occur in many cases, and the significance of measuring the biological information with wearing the device for a long time may disappear. Patent Documents 1 and 2 do not consider the situations.

The present invention has been made in view of the above situations, and an object thereof is to provide a biological information measurement support device, a biological information measurement device, a biological information measurement support method, and a biological information measurement support program capable of supporting efficient measurement of biological information.

Hereinafter, an embodiment of the present invention will be described with reference to the drawings.

Figure 1:
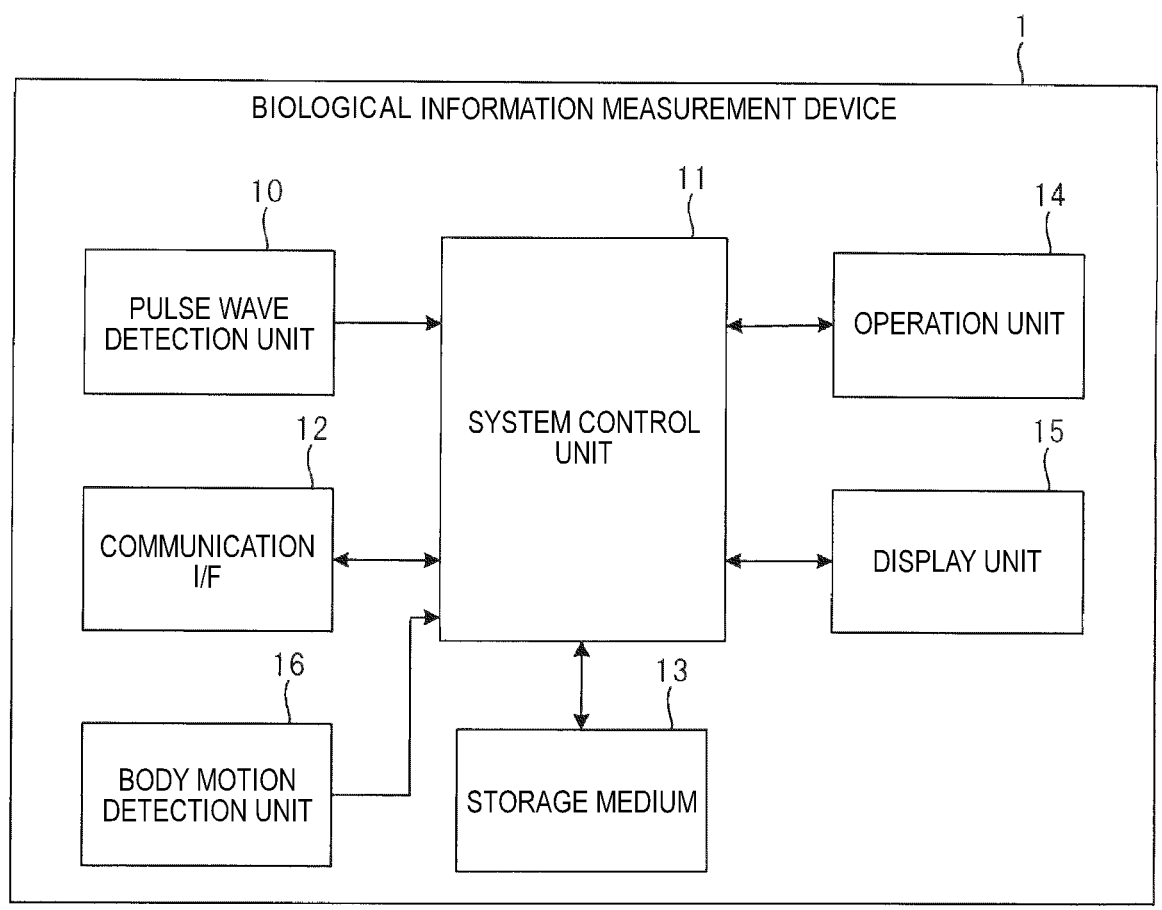
FIG. 1 depicts an internal hardware configuration of a biological information measurement device 1 for illustrating an embodiment of the present invention.

FIG. 1 depicts an internal hardware configuration of a biological information measurement device 1 for illustrating an embodiment of the present invention. The biological information measurement device 1 is used to monitor bedtime biological information of a measurement subject, for example.

The biological information measurement device 1 is to measure and store biological information such as blood pressure information, pulse information, heartbeat information and the like in a storage medium 13. The blood pressure information includes, for example a systolic arterial pressure, a diastolic pressure, an average blood pressure and the like. The pulse information includes, for example, a pulse rate and the like. The heartbeat information includes, for example, a heart rate and the like.

The biological information measurement device 1 includes a pulse wave detection unit 10, a system control unit 11 configured to collectively control the entire device, a communication interface (I/F) 12, a storage medium 13, an operation unit 14, a display unit 15, and a body motion detection unit 16.

The pulse wave detection unit 10 is configured to detect a pulse wave to occur every one pulse from a living body part (for example, a wrist) of the measurement subject and to input the detected pulse wave in the system control unit 11. The pulse wave detection unit 10 is configured to detect a pressure pulse wave as the pulse wave by a tonometry method, for example. The pulse wave detection unit 10 may be configured to detect a volume pulse wave as the pulse wave. The pulse wave detection unit 10 may be configured to detect the pulse wave by reflected light from the artery obtained by irradiating light to the artery.

The system control unit 11 includes a processor, as a main body, and a ROM (Read Only Memory) in which a program and the like to be executed by the processor are stored, a RAM (Random Access Memory) as a work memory, and the like.

The system control unit 11 is configured to calculate biological information based on the pulse wave every one pulse detected by the pulse wave detection unit 10, and to store the calculated biological information in the storage medium 13, in association with date information indicative of a date on which the pulse wave is detected and information of time at which the pulse wave is detected.

The communication I/F 12 is an interface for wired or wireless connection with other electronic devices (for example, a hospital terminal equipped in a hospital).

In the storage medium 13, a variety of data such as the biological information calculated by the system control unit 11 is stored. The storage medium 13 is configured by a flash memory, a hard disk and the like, for example. The storage medium 13 may be a portable type to be detachably mounted to the biological information measurement device 1.

The operation unit 14 is an interface for inputting an instruction signal to the system control unit 11, and is configured by buttons, a touch panel and the like for instructing start or end of diverse operations including measurement of the biological information.

The display unit 15 is to display a variety of information such as the measured biological information, and is configured by a liquid crystal display device or the like, for example.

The body motion detection unit 16 is configured to detect motion of the living body part on which the biological information measurement device 1 is worn, and to input body motion information corresponding to the motion to the system control unit 11. The body motion detection unit 16 is configured by a sensor such as an acceleration sensor, an angular velocity sensor and the like, and a signal processing unit configured to process a signal output from the sensor.

Figure 2:
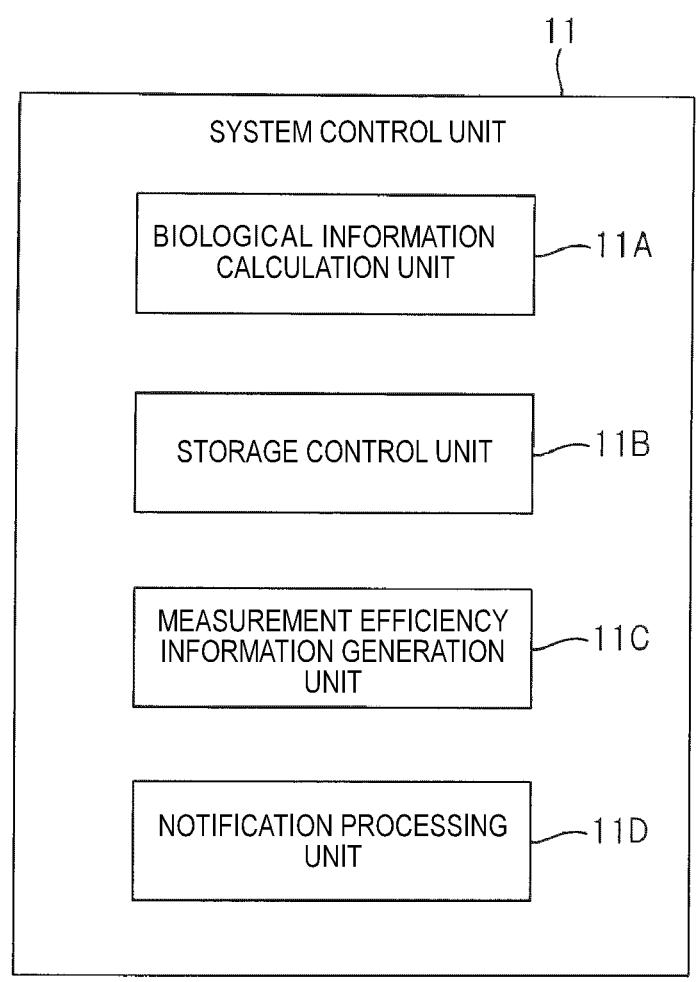
FIG. 2 is a functional block diagram of a system control unit 11 of the biological information measurement device 1 shown in FIG. 1.

FIG. 2 is a functional block diagram of the system control unit 11 of the biological information measurement device 1 shown in FIG. 1.

The system control unit 11 includes a biological information calculation unit 11A, a storage control unit 11B, a measurement efficiency information generation unit 11C, and a notification processing unit 11D. The system control unit 11 configures a biological information measurement support device.

The biological information calculation unit 11A, the storage control unit 11B, the measurement efficiency information generation unit 11C and the notification processing unit 11D are configured as the processor executes the programs stored in the ROM. The programs include a biological information measurement support program.

The biological information calculation unit 11A is configured to calculate the biological information based on the pulse wave input from the pulse wave detection unit 10 by the well-known method. The biological information calculation unit 11A uses the pulse wave detected every one pulse, as the pulse wave of a calculation target of the biological information, but may set a pulse wave detected every other pulse or every multiple pulses, as the calculation target of the biological information.

The biological information calculation unit 11A is configured to store the calculated biological information in the storage medium 13, in association with the information of date and time at which the pulse wave used for the calculation of the biological information is detected. Thereby, in the storage medium 13, the biological information in a unit of one pulse is accumulatively stored.

The biological information calculation unit 11A is configured to calculate the biological information based on the pulse wave input from the pulse wave detection unit 10. However, when an input pulse wave does not satisfy a preset adoption condition, the biological information calculation unit does not calculate the biological information based on the pulse wave, and stores the information of date and time at which the pulse wave is detected in the storage medium 13, in association with measurement failure information indicating that the pulse wave does not satisfy the adoption condition.

Also, when the pulse wave input from the pulse wave detection unit 10 satisfies the adoption condition, the biological information calculation unit 11A calculates the biological information based on the pulse wave, and stores the information of date and time at which the pulse wave is detected and the calculated biological information in the storage medium 13, in association with measurement success information indicating that the pulse wave satisfies the adoption condition.

The adoption condition includes a first condition that the input pulse wave is a pulse wave detected during a body motion stable time period in which a motion amount of the wrist of the measurement subject based on the body motion information detected by the body motion detection unit 16 is smaller than a body motion threshold value, a second condition that a shape of the input pulse wave is a shape capable of calculating the biological information, and the like.

For example, when calculating the pulse rate, it is necessary to calculate time between peaks of the adjacent pulse waves or time between rising times of the adjacent pulse waves. However, when the input pulse wave has a shape incapable of specifying the peak, the rising time and the like, the corresponding pulse wave does not satisfy the adoption condition.

The biological information (the biological information stored with being associated with the measurement success information) calculated based on the pulse wave satisfying the adoption condition by the biological information calculation unit 11A is the biological information of which reliability is equal to or higher than a threshold value.

In the meantime, when the first condition is used as the adoption condition, it may be possible to calculate the biological information based on the pulse wave not satisfying the adoption condition. To this end, in the case of the pulse wave not satisfying the first condition, the biological information calculation unit 11A may calculate the biological information based on the corresponding pulse wave, and store the calculated biological information and the information of date and time at which the pulse wave is detected in the storage medium 13, in association with the measurement failure information.

The storage control unit 11B is configured to store the pulse wave detected by the pulse wave detection unit 10 in the storage medium 13, in association with the information of date and time at which the pulse wave is detected.

Also, the storage control unit 11B is configured to store pulse wave detection time period information, which is information of a time period (a time period from detection start of the pulse wave to detection end) in which pulse wave detection processing has been continuously executed by the pulse wave detection unit 10, in the storage medium 13, in association with a pulse wave group consisting of all the pulse waves detected during the time period.

The pulse wave detection time period information may be any information capable of specifying a length of the time period in which the pulse wave detection processing has been continuously executed. For example, the pulse wave detection time period information may be information indicative of detection start time and detection end time of the time period in which the pulse wave detection processing has been continuously executed, information of a length of the corresponding time period, or the like.

FIG. 3 depicts an example of a data structure of measured data that is to be stored in the storage medium 13 of the biological information measurement device 1 shown in FIG. 1.

The measured data is data including pulse wave detection result information, which indicates a result of the pulse wave detection processing executed over a specific time period by the pulse wave detection unit 10, and biological information calculation result information, which indicates a result of biological information calculation processing executed based on the pulse wave detected by the pulse wave detection processing.

The specific time period is a time period after a measurement start instruction of the biological information is issued to start the detection of the pulse wave and the calculation of the biological information until a measurement ending instruction is issued to end the processing.

When the measurement subject wears the biological information measurement device 1 and measures the biological information during sleep, information ("pulse wave information" in FIG. 3) of the pulse wave detected during the measurement time period, biological information calculated based on the pulse wave, and a measurement flag (information of "1" or "0") indicating whether the pulse wave satisfies the adoption condition are stored in association with date and time ("pulse wave detection date and time" in FIG. 3) at which the pulse wave is detected. The information of date and time of the pulse wave is treated as a detected pulse wave ID, too.

Also, in the storage medium 13, the pulse wave detection time period information (hereinafter, referred to as 'length of the pulse wave detection time period') is stored in association with all the pulse wave IDs detected during the measurement time period.

The measurement flag "1" is information configuring the measurement failure information and indicating that the pulse wave specified by the corresponding ID does not satisfy the adoption condition.

The measurement flag "0" is information configuring the measurement success information and indicating that the pulse wave specified by the corresponding ID satisfies the adoption condition (in other words, information indicating that the reliability of the biological information calculated based on the pulse wave specified by the corresponding ID is equal to or higher than the threshold value).

The pulse wave detection date and time, the pulse wave detection time period information and all the pulse wave information corresponding to the pulse wave detection time period information shown in FIG. 3 configure the pulse wave detection result information indicative of a result of the pulse wave detection processing, respectively.

The pulse wave detection date and time, the biological information and the measurement flag shown in FIG. 3 configure the biological information calculation result information indicative of a calculation result of the biological information made by the biological information calculation unit 11A, respectively.

When a predetermined determination condition is satisfied, the measurement efficiency information generation unit 11C generates information (hereinafter, referred to as 'measurement efficiency information') indicative of a measurement efficiency of the biological information included in the measured data, based on the measured data (FIG. 3) stored in the storage medium 13.

The determination condition includes a condition that a measurement ending button included in the operation unit 14 is pushed to instruct measurement ending of the biological information, a condition that a measurement efficiency confirmation button included in the operation unit 14 is pushed to instruct notification of the measurement efficiency information, and the like, for example.

Also, when the biological information measurement device 1 is operated by a battery, a determination condition that a remaining battery level of the biological information measurement device 1 is equal to or less than a predetermined remaining level threshold value necessary to perform a measurement operation of the biological information may be adopted.

Also, when the biological information measurement device 1 includes a body motion detection unit such as an acceleration sensor and a sleep determination unit configured to determine a sleep state of the measurement subject wearing the biological information measurement device 1 based on the body motion information detected by the body motion detection unit, a determination condition that the measurement subject has shifted from the sleep state to an awakening state (wake-up state) may be adopted.

The measurement efficiency of the biological information is an index indicating how the biological information having the reliability equal to or higher than the threshold value could be stored in the storage medium 13 without waste for a time period after the measurement start instruction of the biological information is issued to start the measurement operation (detection of the pulse wave and calculation and storing of the biological information based on the pulse wave) until the determination condition is satisfied. The method of generating the measurement efficiency information by the measurement efficiency information generation unit 11C will be described in detail later.

The notification processing unit 11D is configured to execute processing of notifying the measurement efficiency information generated by the measurement efficiency information generation unit 11C.

The processing includes processing of displaying the measurement efficiency information on the display unit 15, processing of outputting the measurement efficiency information from a speaker (not shown) of the biological information measurement device 1 with a voice, processing of transmitting the measurement efficiency information from the communication I/F 12 to an external electronic device (for example, a smart phone carried by the measurement subject), and the like.

Subsequently, specific examples of the method of generating the measurement efficiency information by the measurement efficiency information generation unit 11C are described. The measurement efficiency information generation unit 11C generates the measurement efficiency information by any one of following methods.

(First Measurement Efficiency Information Generation Method)

The measurement efficiency information generation unit 11C generates, as the measurement efficiency information, image information indicative of a distribution of time periods, in which pulse waves becoming a calculation source of the biological information having the reliability equal to or higher than the threshold value (the biological information for which the measurement flag is set as "0") have been detected, in the pulse wave detection time period indicated by the pulse wave detection time period information, based on the measured data shown in FIG. 3.

The time period in which any pulse wave is detected indicates a time period from detection time of the corresponding pulse wave to detection time of a pulse wave detected immediately before or after the corresponding pulse wave.

In the case where the first measurement efficiency information generation method is adopted, the pulse wave information of the measured data shown in FIG. 3 is not necessarily required.

Figure 4:
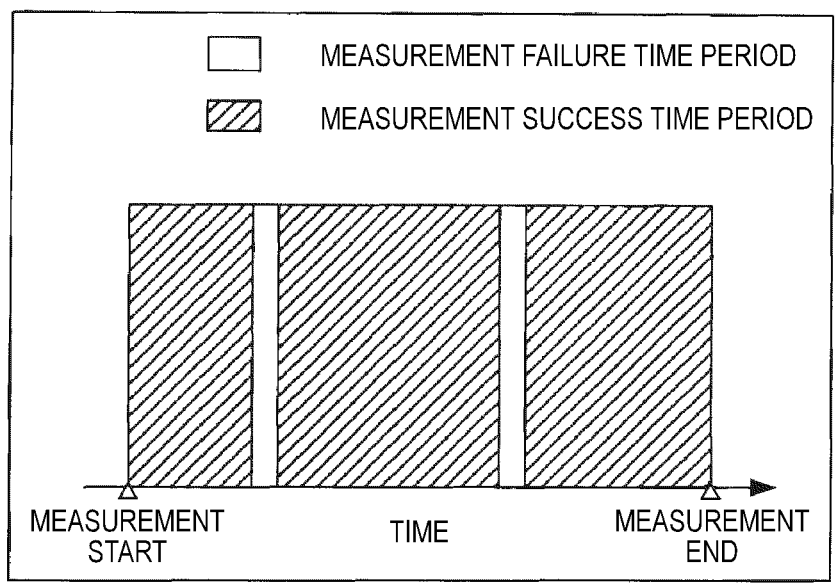
FIG. 4 depicts a screen example in which an image based on image information generated by a first measurement efficiency information generation method is displayed on a display unit 15.

FIG. 4 depicts a screen example in which an image based on the image information generated by the first measurement efficiency information generation method is displayed on the display unit 15.

In the screen shown in FIG. 4, the pulse wave detection time period is shown with a rectangular shape in which a horizontal axis indicates time. A time period (measurement success time period) in which the pulse waves becoming a calculation source of the biological information corresponding to the measurement flag "0" have been detected and the other time period (a time period (measurement failure time period) in which the pulse waves becoming a calculation source of the biological information corresponding to the measurement flag "1" have been detected) are shown with different colors.

(Second Measurement Efficiency Information Generation Method)

The measurement efficiency information generation unit 11C generates, as the measurement efficiency information, information indicative of a relation of a length of a cumulative time period of the time periods, in which pulse waves becoming a calculation source of the biological information having the reliability equal to or higher than the threshold value (the biological information for which the measurement flag is set as "0") have been detected, to a length of the pulse wave detection time period indicated by the pulse wave detection time period information, based on the measured data shown in FIG. 3. This information may be any information with which it is possible to know the relation of the two lengths, and is a ratio of the two lengths, for example.

Alternatively, the measurement efficiency information generation unit 11C generates, as the measurement efficiency information, information indicative of a relation of a length of a cumulative time period of time periods other than the time periods, in which pulse waves becoming a calculation source of the biological information having the reliability equal to or higher than the threshold value (the biological information for which the measurement flag is set as "0") have been detected, to a length of the pulse wave detection time period indicated by the pulse wave detection time period information, based on the measured data shown in FIG. 3.

In the case where the second measurement efficiency information generation method is adopted, the pulse wave information of the measured data shown in FIG. 3 is not necessarily required.

Figure 5:
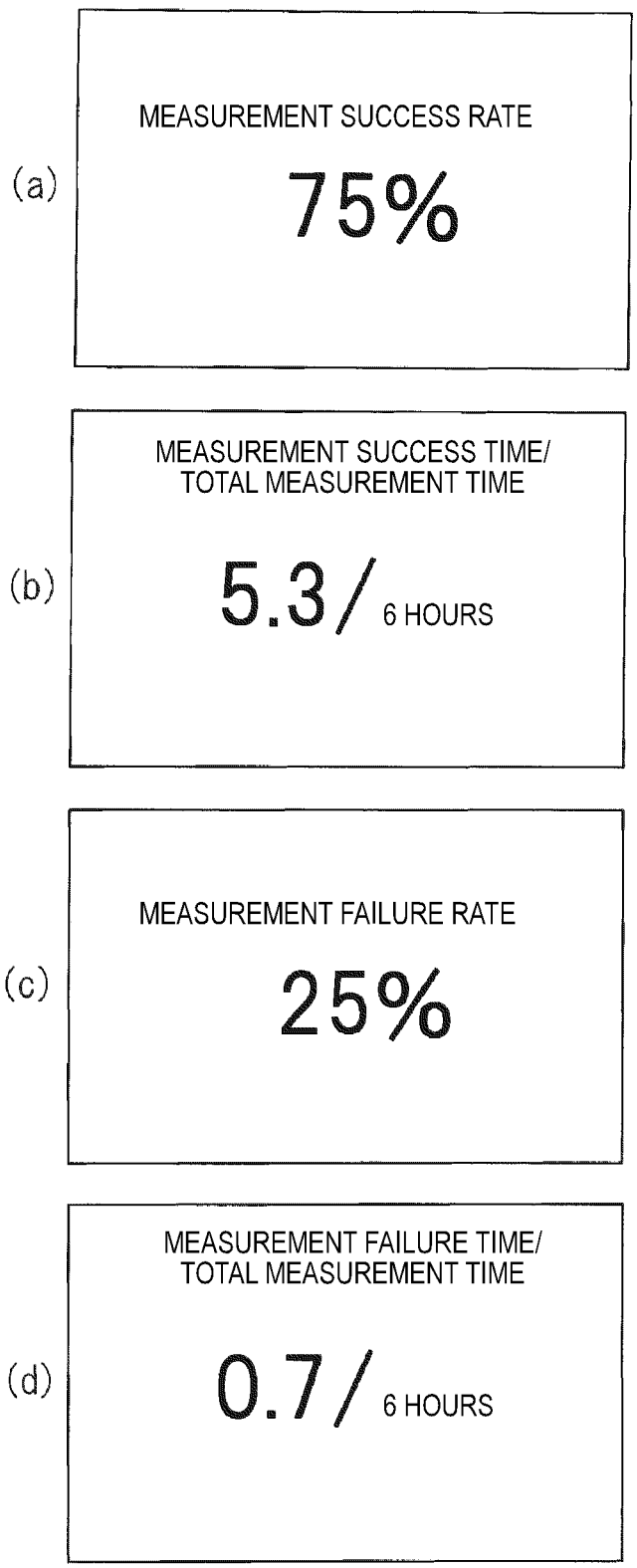
FIG. 5 depicts a screen example in which an image based on information generated by a second measurement efficiency information generation method is displayed on the display unit 15.

FIG. 5 depicts a screen example in which an image based on the information generated by the second measurement efficiency information generation method is displayed on the display unit 15.

In the screen shown in (a) of FIG. 5, the characters "measurement success rate 75%" indicative of a ratio of the length of the cumulative time period of the time periods, in which the pulse waves corresponding to the measurement flag "0" have been detected, to the length of the pulse wave detection time period are shown as the measurement efficiency information.

In the screen shown in (b) of FIG. 5, the characters "5.3/6 hours" indicative of a ratio of the length (measurement success time) of the cumulative time period of the time periods, in which the pulse waves corresponding to the measurement flag "0" have been detected, to the length (total measurement time) of the pulse wave detection time period are shown as the measurement efficiency information.

In the screen shown in (c) of FIG. 5, the characters "measurement failure rate 25%" indicative of a ratio of the length of the cumulative time period of the time periods, in which the pulse waves corresponding to the measurement flag "1" have been detected, to the length of the pulse wave detection time period are shown as the measurement efficiency information.

In the screen shown in (d) of FIG. 5, the characters "0.7/6 hours" indicative of a ratio of the length (measurement failure time) of the cumulative time period of the time periods, in which the pulse waves corresponding to the measurement flag "1" have been detected, to the length (total measurement time) of the pulse wave detection time period are shown as the measurement efficiency information.

Figure 6:
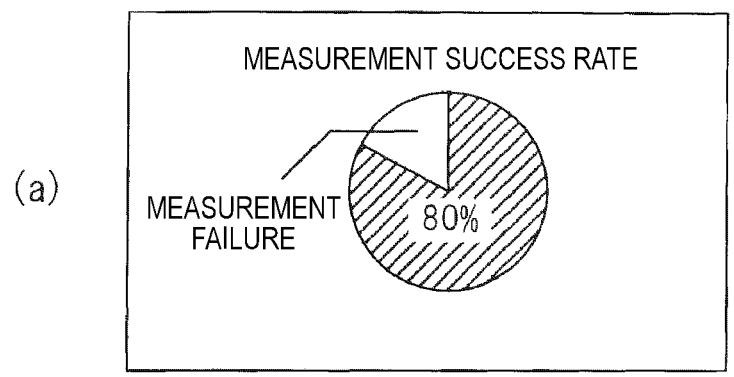
FIG. 6 depicts another screen example in which an image based on information generated by the second measurement efficiency information generation method is displayed on the display unit 15.
Figure 6:
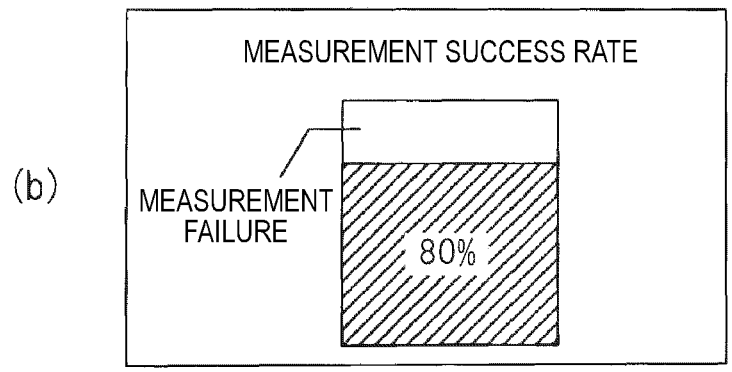

FIG. 6 depicts another screen example in which an image based on the information generated by the second measurement efficiency information generation method is displayed on the display unit 15.

In the screens shown in (a) and (b) of FIG. 6, a circle graph or a bar graph indicative of a ratio of the length of the cumulative time period of the time periods, in which the pulse waves corresponding to the measurement flag "0" have been detected, to the length of the pulse wave detection time period are shown as the measurement efficiency information.

(Third Measurement Efficiency Information Generation Method)

The measurement efficiency information generation unit 11C divides the pulse wave detection time period indicated by the pulse wave detection time period information into multiple time periods, and generates, as the measurement efficiency information, information indicative of a relation of a length of a cumulative time period of time periods, in which pulse waves becoming a calculation source of the biological information of which the reliability corresponding to each divided time period is equal to or higher than the threshold value have been detected, to a length of each divided time period, based on the measured data shown in FIG. 3.

Alternatively, the measurement efficiency information generation unit 11C divides the pulse wave detection time period indicated by the pulse wave detection time period information into multiple time periods, and generates, as the measurement efficiency information, information indicative of a relation of a length of a time period other than the cumulative time period of the time periods, in which pulse waves becoming a calculation source of the biological information of which the reliability corresponding to each divided time period is equal to or higher than the threshold value (the biological information for which the measurement flag is set as "0") have been detected, to a length of each divided time period, based on the measured data shown in FIG. 3.

In the case where the third measurement efficiency information generation method is adopted, the pulse wave information of the measured data shown in FIG. 3 is not necessarily required.

Figure 7:
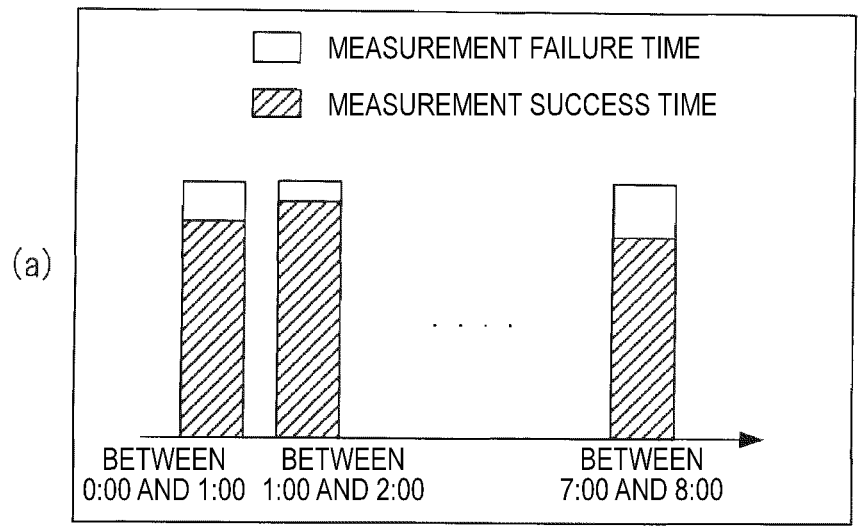
FIG. 7 depicts a screen example in which an image based on information generated by a third measurement efficiency information generation method is displayed on the display unit 15.
Figure 7:
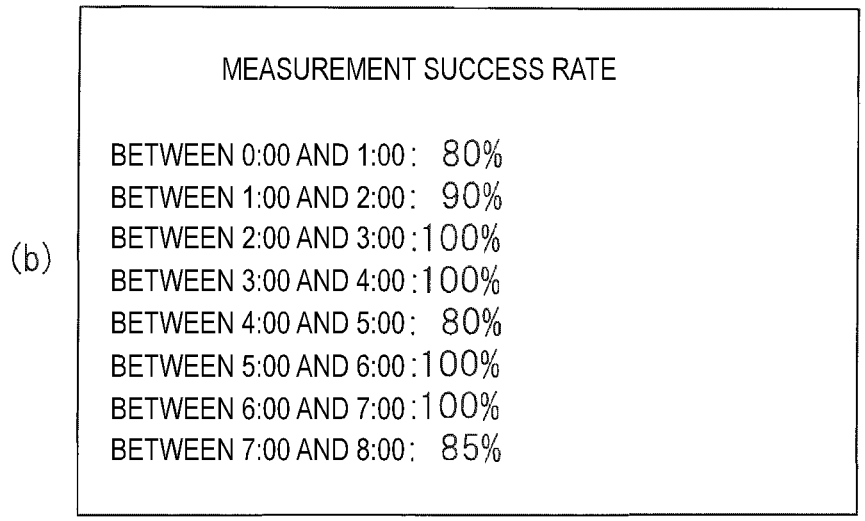
Figure 7:
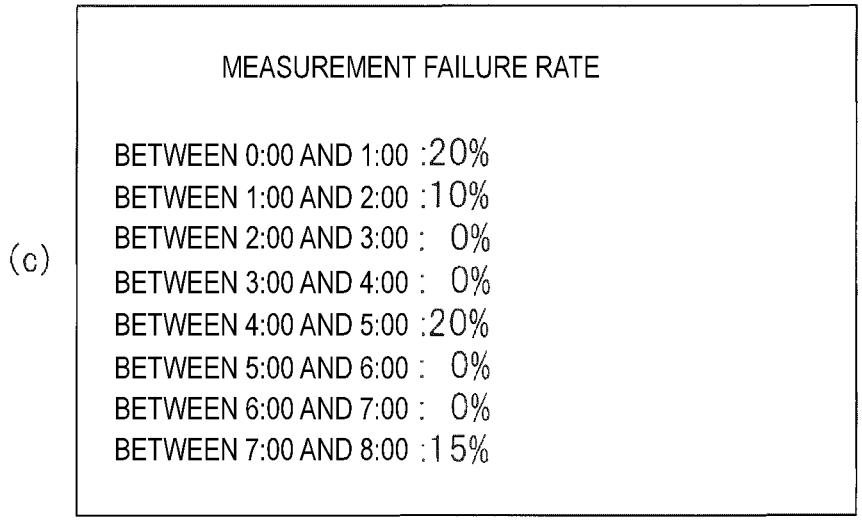

FIG. 7 depicts a screen example in which an image based on the information generated by the third measurement efficiency information generation method is displayed on the display unit 15. FIG. 7 depicts a display example in which the pulse wave detection time period is A.M. 0:00 to A.M. 08:00 and the pulse wave detection time period is divided into 8 periods in a unit of one hour.

In the screen shown in (a) of FIG. 7, each divided time period is shown with a rectangular shape in which a horizontal axis indicates time. In the rectangle indicating each divided time period, a length (measurement success time period) of the time period in which the pulse waves becoming a calculation source of the biological information corresponding to the measurement flag "0" have been detected and a length of the other time period (measurement failure time period) are shown with different colors.

In the screen shown in (b) of FIG. 7, for each divided time period, a measurement success rate (a ratio of the cumulative time of the time periods, in which the pulse waves corresponding to the measurement flag "0" have been detected, to the total measurement time) is shown. In the screen shown in (c) of FIG. 7, for each divided time period, a measurement failure rate (a ratio of the cumulative time of the time periods, in which the pulse waves corresponding to the measurement flag "1" have been detected, to the total measurement time) is shown.

(Fourth Measurement Efficiency Information Generation Method)

The measurement efficiency information generation unit 11C calculates a total number of the pulse waves detected during the pulse wave detection time period indicated by the pulse wave detection time period information and a total number (total number of the measurement flag "0") of the biological information of which the reliability included in the measured data is equal to or higher than the threshold value, respectively, based on the measured data shown in FIG. 3. Then, the measurement efficiency information generation unit 11C generates, as the measurement efficiency information, a ratio (measurement success rate) of the total number of the measurement flag "0" to the total number of the pulse waves. In the meantime, the number of intervals of the adjacent pulse waves to the pulse waves detected during the pulse wave detection time period may be treated as the total number of the pulse waves detected during the pulse wave detection time period.

Alternatively, the measurement efficiency information generation unit 11C calculates a total number of the pulse waves detected during the pulse wave detection time period indicated by the pulse wave detection time period information and a total number (total number of the measurement flag "1") of the pulse waves other than the pulse waves becoming a calculation source of the biological information having the reliability equal to or higher than the threshold value of the pulse waves detected during the pulse wave detection time period, respectively, based on the measured data shown in FIG. 3. Then, the measurement efficiency information generation unit 11C generates, as the measurement efficiency information, a ratio (measurement failure rate) of the total number of the measurement flag "1" to the total number of the pulse waves.

In the case where the fourth measurement efficiency information generation method is adopted, the information of the total number of the pulse waves detected during the pulse wave detection time period may be stored, instead of all the pulse wave information of the measured data shown in FIG. 3.

FIG. 8 depicts a screen example in which an image based on the information generated by the fourth measurement efficiency information generation method is displayed on the display unit 15.

In the screen shown in (a) of FIG. 8, the characters "measurement success rate 80%" indicative of a ratio of the total number of the measurement flag "0" to the total number of the pulse waves detected during the pulse wave detection time period indicted by the pulse wave detection time period information are shown as the measurement efficiency information.

In the screen shown in (b) of FIG. 8, the characters "24,000/30,000" indicative of a ratio of the total number (the number of valid data) of the measurement flag "0" to the total number (the total number of data) of the pulse waves detected during the pulse wave detection time period indicted by the pulse wave detection time period information are shown as the measurement efficiency information.

In the screen shown in (c) of FIG. 8, the characters "measurement failure rate 20%" indicative of a ratio of the total number of the measurement flag "1" to the total number of the pulse waves detected during the pulse wave detection time period indicted by the pulse wave detection time period information are shown as the measurement efficiency information.

In the screen shown in (d) of FIG. 8, the characters "6,000/30,000" indicative of a ratio of the total number (the number of invalid data) of the measurement flag "1" to the total number (the total number of data) of the pulse waves detected during the pulse wave detection time period indicted by the pulse wave detection time period information are shown as the measurement efficiency information.

In the meantime, as shown in FIG. 6, the measurement efficiency information may be shown by the graph.

(Fifth Measurement Efficiency Information Generation Method)

The measurement efficiency information generation unit 11C divides the pulse wave detection time period indicated by the pulse wave detection time period information into multiple time periods, and generates the total number of the pulse waves detected in each divided time period and the total number (total number of the measurement flag "0") of the biological information of which the reliability corresponding to each divided time period is equal to or higher than the threshold value, respectively, based on the measured data shown in FIG. 3. The measurement efficiency information generation unit 11C generates, as the measurement efficiency information, a ratio (measurement success rate) of the total number of the measurement flag "0" in each divided time period to the total number of the pulse waves in each divided time period.

Alternatively, the measurement efficiency information generation unit 11C divides the pulse wave detection time period indicated by the pulse wave detection time period information into multiple time periods, and generates the total number of the pulse waves detected in each divided time period and a value (total number of the measurement flag "1" corresponding to each divided time period) obtained by subtracting the total number of the biological information of which the reliability corresponding to each divided time period is equal to or higher than the threshold value from the total number of the pulse waves in each divided time period, respectively, based on the measured data shown in FIG. 3. The measurement efficiency information generation unit 11C generates, as the measurement efficiency information, a ratio (measurement failure rate) of the total number of the measurement flag "1" in each divided time period to the total number of the pulse waves in each divided time period.

In the case where the fifth measurement efficiency information generation method is adopted, the pulse wave information of the measured data shown in FIG. 3 is not necessarily required. Also, instead of the pulse wave information of the measured data shown in FIG. 3, the information of the total number in each divided time period of the pulse wave information may be stored.

The display examples of the image based on the information generated by the fifth measurement efficiency information generation method are as shown in (a) and (b) of FIG. 7.

(Sixth Measurement Efficiency Information Generation Method)

The measurement efficiency information generation unit 11C estimates the total number of the pulse waves detected in the pulse wave detection time period indicated by the pulse wave detection time period information, based on some pulse wave information (for example, the pulse wave information for one minute) of all the pulse wave information included in the measured data of FIG. 3 and the pulse wave detection time period information included in the measured data of FIG. 3.

The measurement efficiency information generation unit 11C calculates the number of the pulse waves detected in the pulse wave detection time period indicated by the pulse wave detection time period information from the number of the pulse waves detected in a unit time period.

For example, when the number of the pulse wave information detected for one minute and included in the measured data is "50" and the pulse wave detection time period indicated by the pulse wave detection time period information included in the measured data is 420 minutes, it is possible to estimate the total number of the pulse waves in the corresponding pulse wave detection time period by calculation of 50×420=21000.

Also, the measurement efficiency information generation unit 11C calculates the total number (the number of the measurement flag "0") of the biological information of which reliability included in the measured data is equal to or higher than the threshold value. Then, the measurement efficiency information generation unit 11C generates, as the measurement efficiency information, a ratio (measurement success rate) of the calculated total number of the measurement flag "0" to the estimated total number of the pulse waves. Alternatively, the measurement efficiency information generation unit 11C generates, as the measurement efficiency information, a ratio (measurement failure rate) of the total number of the measurement flag "1" to the estimated total number of the pulse waves.

In the case where the sixth measurement efficiency information generation method is adopted, regarding the pulse wave information in the measured data of FIG. 3, only data of predetermined unit time period may be stored. Alternatively, instead of the pulse wave information, the information of the total number of the pulse waves detected in a unit time period may be stored.

(Seventh Measurement Efficiency Information Generation Method)

The measurement efficiency information generation unit 11C estimates the total number of the pulse waves detected in the pulse wave detection time period by a method similar to the sixth measurement efficiency information generation method.

Also, the measurement efficiency information generation unit 11C divides the pulse wave detection time period indicated by the pulse wave detection time period information into multiple periods, and calculates the total number of the pulse waves estimated as being detected in each divided time period and the total number (the total number of the measurement flag "0") of the biological information of which the reliability corresponding to each divided time period is equal to or higher than the threshold value, respectively.

The measurement efficiency information generation unit 11C obtains the total number of the pulse waves estimated as being detected in the divided time period by dividing the total number of the pulse waves in the pulse wave detection time period, which is estimated by the above method, by the number of the divided time periods.

The measurement efficiency information generation unit 11C generates, as the measurement efficiency information, a ratio (measurement success rate) of the total number of the measurement flag "0" corresponding to each divided time period to the estimated total number of the pulse waves in each divided time period. Alternatively, the measurement efficiency information generation unit 11C generates, as the measurement efficiency information, a ratio (measurement failure rate) of the total number of the measurement flag "1" corresponding to each divided time period to the estimated total number of the pulse waves in each divided time period.

The display examples of the image based on the information generated by the seventh measurement efficiency information generation method are as shown in (b) and (c) of FIG. 7.

In the case where the seventh measurement efficiency information generation method is adopted, regarding the pulse wave information in the measured data of FIG. 3, only data of predetermined unit time period may be stored. Alternatively, instead of the pulse wave information, the information of the total number of the pulse waves detected in a unit time period may be stored.

Figure 9:
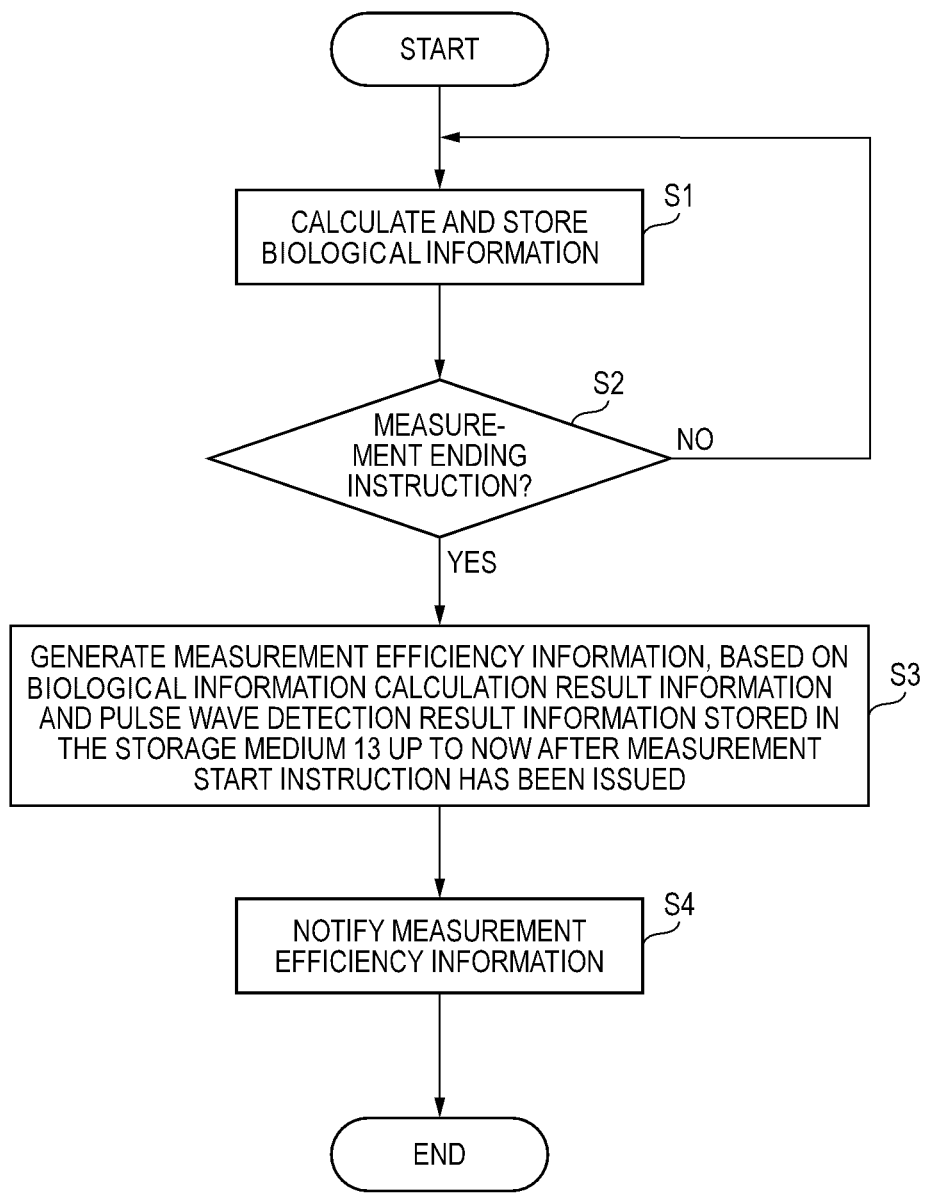
FIG. 9 is a flowchart depicting operations of the biological information measurement device 1 shown in FIG. 1.

FIG. 9 is a flowchart depicting operations of the biological information measurement device 1 shown in FIG. 1.

When the operation unit 14 is operated to issue a measurement start instruction of the biological information, the pulse wave detection unit 10 starts pulse wave detection processing. The pulse wave detected by the pulse wave detection processing is stored in the storage medium 13, in association with the information of date and time. When the pulse wave detection processing starts, the system control unit 11 executes processing of calculating and storing the biological information based on the pulse wave detected by the pulse wave detection unit 10 (step S1).

After starting the calculation processing of the biological information, the system control unit 11 determines whether a measurement ending instruction of the biological information has been issued (step S2). When the measurement ending instruction has not been issued (step S2: NO), the processing returns to step S1.

On the other hand, when the measurement ending instruction has been issued (step S2: YES), the system control unit 11 stops the pulse wave detection unit 10, ends the calculation processing of the biological information, and generates the measurement efficiency information indicative of the measurement efficiency of the biological information included in the biological information calculation result information, based on the biological information calculation result information and the pulse wave detection result information stored in the storage medium 13 up to now after the measurement start instruction has been issued (step S3). The generation of the measurement efficiency information is performed by any one of the first to seventh methods.

Then, the system control unit 11 displays the generated measurement efficiency information on the display unit 15, thereby notifying the same to a user of the biological information measurement device 1 (step S4).

Here, the processing of step S3 and thereafter is executed when the measurement ending instruction has been issued. However, when a notification instruction of the measurement efficiency information is issued during the measurement of the biological information or while the biological information is not measured, the system control unit 11 may generate the measurement efficiency information based on the latest measured data stored in the storage medium 13, and notify the generated measurement efficiency information.

Also, in the case where the system control unit 11 is operated by the battery, when a remaining battery level of the biological information measurement device 1 is equal to or less than a remaining level threshold value necessary to perform the measurement operation of the biological information, the system control unit 11 executes the processing of step S3 and thereafter, and then turns off a power supply of the device.

Like this, according to the biological information measurement device 1, the user of the biological information measurement device 1 can recognize the measured measurement efficiency of the biological information at timing such as upon measurement end of the biological information. For this reason, when the measurement efficiency is low, it is possible to take measures to reduce the body motion, for example, so that it is possible to efficiently measure the biological information. As a result, it is possible to provide the device capable of efficiently obtaining the biological information, which is necessary for a doctor to make a diagnosis, and having merits for both the doctor and a patient.

Also, according to the biological information measurement device 1, when the measurement ending instruction of the biological information has been issued, for example, the measurement efficiency information is notified. For this reason, the measurement subject can immediately check the measurement efficiency information of the biological information, which was measured during the sleep, for example, after the wake-up. Thereby, it is possible to make an action plan for improving the measurement efficiency while the memory is fresh.

Also, according to the biological information measurement device 1, when the notification instruction of the measurement efficiency information has been issued, the measurement efficiency information is notified. For this reason, the measurement subject can check the measurement notification information at any timing, so that it is possible to improve the convenience.

Also, according to the first measurement efficiency information generation method, as shown in FIG. 4, it is possible to intuitively perceive when the measurement has failed. For this reason, it is possible to easily determine a cause of the lowering in the measurement efficiency, and to easily take measures for improving the measurement efficiency.

Also, according to the first measurement efficiency information generation method and the second measurement efficiency information generation method, it is possible to generate the measurement efficiency information without using the pulse wave information. For this reason, it is possible to save the power necessary to store the pulse wave information and to prevent the increase in capacity of the storage medium 13, so that it is possible to implement the energy saving and the cost reduction.

Also, according to the third measurement efficiency information generation method, it is possible to perceive the measurement efficiency in each divided time period. For this reason, it is possible to easily determine a cause of the lowering in the measurement efficiency, and to easily take measures for improving the measurement efficiency. Also, according to the third measurement efficiency information generation method, it is possible to generate the measurement efficiency information without using the pulse wave information. For this reason, it is possible to save the power necessary to store the pulse wave information and to prevent the increase in capacity of the storage medium 13 necessary to store the pulse wave information, so that it is possible to implement the energy saving and the cost reduction.

Also, according to the fourth measurement efficiency information generation method, it is possible to generate the measurement efficiency information without using the pulse wave information. For this reason, it is possible to save the power necessary to store the pulse wave information and to prevent the increase in capacity of the storage medium 13 necessary to store the pulse wave information, so that it is possible to implement the energy saving and the cost reduction.

Also, according to the fifth measurement efficiency information generation method, it is possible to perceive the measurement efficiency in each divided time period. For this reason, it is possible to easily determine a cause of the lowering in the measurement efficiency, and to easily take measures for improving the measurement efficiency. Also, according to the fifth measurement efficiency information generation method, it is possible to generate the measurement efficiency information without using the pulse wave information. For this reason, it is possible to save the power necessary to store the pulse wave information and to prevent the increase in capacity of the storage medium 13 necessary to store the pulse wave information, so that it is possible to implement the energy saving and the cost reduction.

Also, according to the sixth measurement efficiency information generation method, it is possible to generate the measurement efficiency information by adopting, as the pulse wave information, the pulse wave information in a unit time period or the information of the total number of the pulse waves detected in a unit time period. For this reason, it is possible to save the power necessary to store the pulse wave information and to prevent the increase in capacity of the storage medium 13 necessary to store the pulse wave information, so that it is possible to implement the energy saving and the cost reduction.

Also, according to the seventh measurement efficiency information generation method, it is possible to perceive the measurement efficiency in each divided time period. For this reason, it is possible to easily determine a cause of the lowering in the measurement efficiency, and to easily take measures for improving the measurement efficiency. Also, according to the seventh measurement efficiency information generation method, it is possible to generate the measurement efficiency information by using the pulse wave information in a unit time period or the information of the total number of the pulse waves detected in a unit time period. For this reason, it is possible to save the power necessary to store the pulse wave information and to prevent the increase in capacity of the storage medium 13 necessary to store the pulse wave information, so that it is possible to implement the energy saving and the cost reduction.

In the meantime, when the measurement efficiency information generation unit 11C executes the processing of step S3 and thereafter at a point of time at which the measurement ending instruction or the notification instruction has been issued, the biological information, which has been calculated up to a point of time before a predetermined time period from the point of time and stored in the storage medium 13, of the biological information included in the measured data is preferably excluded from the biological information that is to be used for generation of the measurement efficiency information.

The measurement ending instruction or the notification instruction is input to the system control unit 11 by operating the operation unit 14. For example, when the biological information measurement device 1 is worn on the wrist, a noise due to the body motion may be superimposed on the pulse wave by a hand operation for operating the operation unit 14. When the measurement efficiency information is generated with the pulse wave having the noise superimposed thereon being included, the measurement efficiency may be lowered below an actual value.

For this reason, the pulse wave detected for a time period in which the noise is likely to be generated, such as an operating time period of the operation unit 14, and the biological information calculated based on the pulse wave are excluded from the measured data, so that it is possible to obtain the more correct measurement efficiency information.

Likewise, the measurement efficiency information generation unit 11C preferably excludes the biological information, which has been calculated up to a point of time after a predetermined time period has elapsed from the issuance of the measurement start instruction and was stored in the storage medium 13, of the biological information included in the measured data from the biological information that is to be used for generation of the measurement efficiency information.

When it is assumed that the biological information measurement device 1 is used during the sleep, the predetermined time is preferably time after the measurement start instruction has been issued until a change amount in the body motion of the measurement subject wearing the biological information measurement device 1 enters a predetermined range. That is, the measurement efficiency information generation unit 11C preferably excludes the biological information, which has been calculated for the time period after the measurement start instruction has been issued until a change amount in the body motion of the measurement subject enters a predetermined range and stored in the storage medium 13, of the biological information included in the measured data from the biological information that is to be used for generation of the measurement efficiency information. Like this, the pulse wave generated due to the motion of the measurement subject during the sleep and the biological information calculated based on the pulse wave are excluded from the measured data, so that it is possible to obtain the more correct measurement efficiency information.

In the case where the adoption condition is the first condition, when the pulse wave specified with any pulse wave ID does not satisfy the adoption condition, the biological information calculation unit 11A preferably store the measurement flag "1" and information (information indicating the measurement failure due to the body motion) indicating a cause due to which the pulse wave does not satisfy the adoption condition, in association with the pulse wave ID.

In the case where a plurality of the pulse waves for which the measurement flag "1" is stored is continuously detected, when the number of the continuously detected pulse waves is equal to or larger than a first threshold value and is smaller than a second threshold value, the biological information calculation unit 11A determines that the cause due to which the plurality of pulse waves does not satisfy the adoption condition is "unconscious body motion" such as rolling over. Then, the biological information calculation unit 11A stores the information, which indicates that the adoption condition is not satisfied due to "unconscious body motion", in association with the plurality of pulse waves.

When the number of the continuously detected pulse waves is equal to or larger than the second threshold value, the biological information calculation unit 11A determines that the cause due to which the plurality of pulse waves does not satisfy the adoption condition is "conscious movement" such as night-time movement to a toilet. Then, the biological information calculation unit 11A stores the information, which indicates that the adoption condition is not satisfied due to "conscious movement", in association with the plurality of pulse waves.

It is thought that the unconscious body motion such as 'rolling over' occurs in a short time and the conscious movement such as 'movement to a toilet' continues longer than 'rolling over'. For this reason, it is possible to determine the cause of the body motion, based on the number of continuous pulse waves when the pulse waves for which the measurement flag "1" is stored continue.

Then, when notifying the measurement efficiency information, the measurement efficiency information generation unit 11C notifies the information, too, which indicates the cause due to which the pulse wave does not satisfy the adoption condition.

Figure 10:
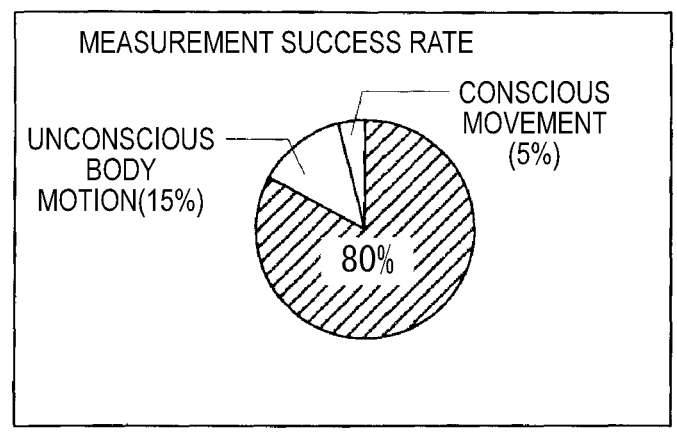
FIG. 10 depicts an example in which both measurement efficiency information and a cause of measurement failure are displayed.
Figure 10:
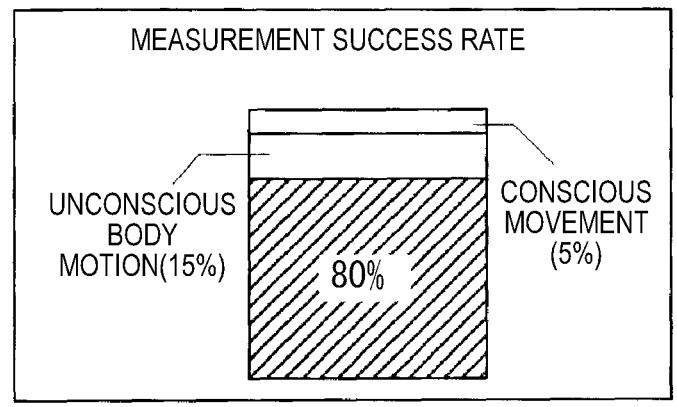

For example, when displaying the image shown in FIG. 6 on the display unit 15, the cause of the measurement failure is displayed with being divided into the unconscious body motion and the conscious movement, as shown in FIG. 10. Specifically, for each cause of the measurement failure, a ratio of the pulse waves, which do not satisfy the adoption condition, to the total number of the pulse waves or a ratio of a length of a cumulative time period of time periods, in which the pulse waves not satisfying the adoption condition have been detected, to the pulse wave detection time period is calculated, and the ratio is displayed together with the measurement efficiency information.

Figure 11:
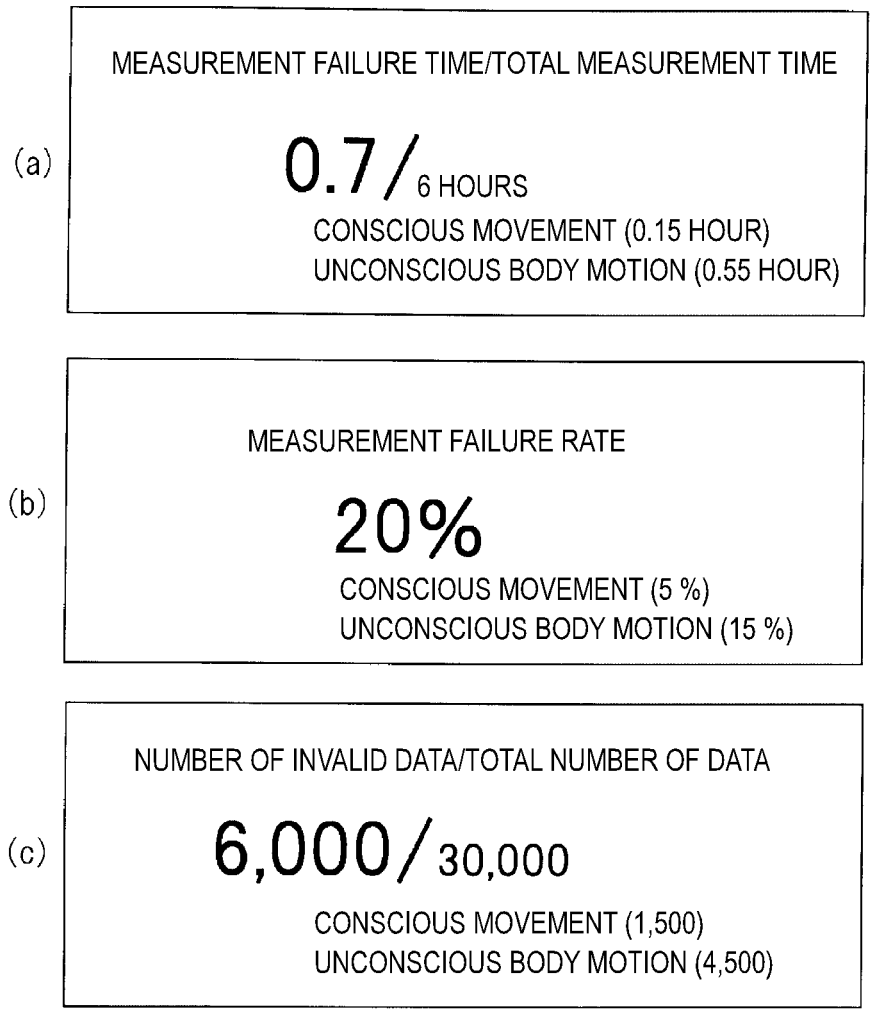
FIG. 11 depicts an example in which both the measurement efficiency information and a cause of the measurement failure are displayed.

Also in the screen examples of FIG. 4, (c) of FIG. 5, (d) of FIG. 5, (c) of FIG. 8 or (d) of FIG. 8, the cause of the measurement failure may be displayed, as exemplified in FIG. 11.

In this way, the cause of the measurement failure of the biological information is notified, so that the user of the biological information measurement device 1 can easily perceive an action to be taken so as to increase the measurement efficiency.

Figure 12:
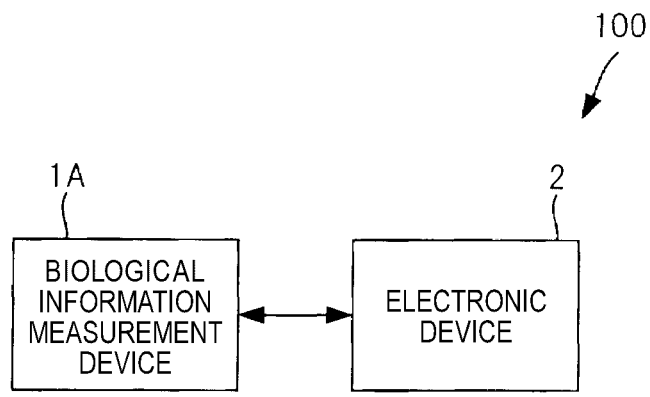
FIG. 12 depicts a schematic configuration of a diagnosis support system 100, which is an embodiment of the present invention.

FIG. 12 depicts a schematic configuration of a diagnosis support system 100, which is an embodiment of the present invention. The diagnosis support system 100 includes a biological information measurement device 1A, and an electronic device 2.

Since an internal hardware configuration of the biological information measurement device 1A is the same as the biological information measurement device 1, the descriptions thereof are omitted. In a functional block diagram of the system control unit 11 of the biological information measurement device 1A, the measurement efficiency information generation unit 11C and the notification processing unit 11D of FIG. 2 are omitted.

The electronic device 2 is an electronic device such as a personal computer, a smart phone, a table terminal or the like.

The electronic device 2 can be connected to the biological information measurement device 1A in a wired or wireless manner, and can read the data in the storage medium 13 of the biological information measurement device 1A. In the meantime, when the storage medium 13 of the biological information measurement device 1A is a portable type, the electronic device 2 has a means capable of reading the data from the storage medium, and may be configured to read the data from the mounted storage medium.

Figure 13:
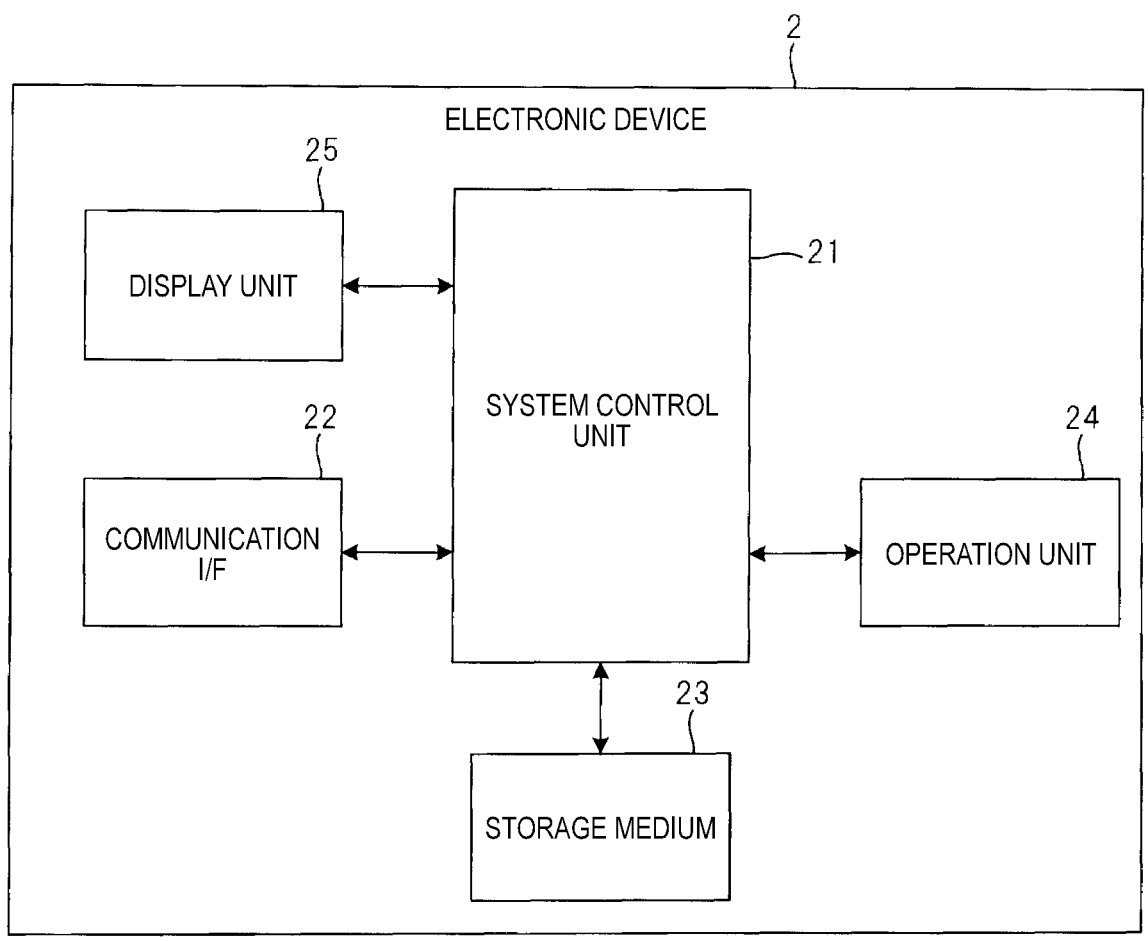
FIG. 13 depicts an internal hardware configuration of an electronic device 2 of the diagnosis support system 100 shown in FIG. 12.

FIG. 13 depicts an internal hardware configuration of the electronic device 2 of the diagnosis support system 100 shown in FIG. 12.

The electronic device 2 includes a system control unit 21 configured to collectively control the entire device, a communication interface (I/F) 22, a storage medium 23, an operation unit 24, and a display unit 25.

The system control unit 21 includes a processor, as a main body, and a ROM in which a program and the like to be executed by the processor are stored, a RAM as a work memory, and the like.

The communication I/F 22 is an interface for wired or wireless connection with an electronic device including the biological information measurement device 1A.

In the storage medium 23, the data read out from the biological information measurement device 1A is stored. The storage medium 23 is configured by a flash memory and the like, for example.

The operation unit 24 is an interface for inputting an instruction signal to the system control unit 21, and is configured by a keyboard, a mouse, a button, a touch panel or the like.

The display unit 25 is to display a variety of information and is configured by a liquid crystal display device or the like, for example.

Figure 14:
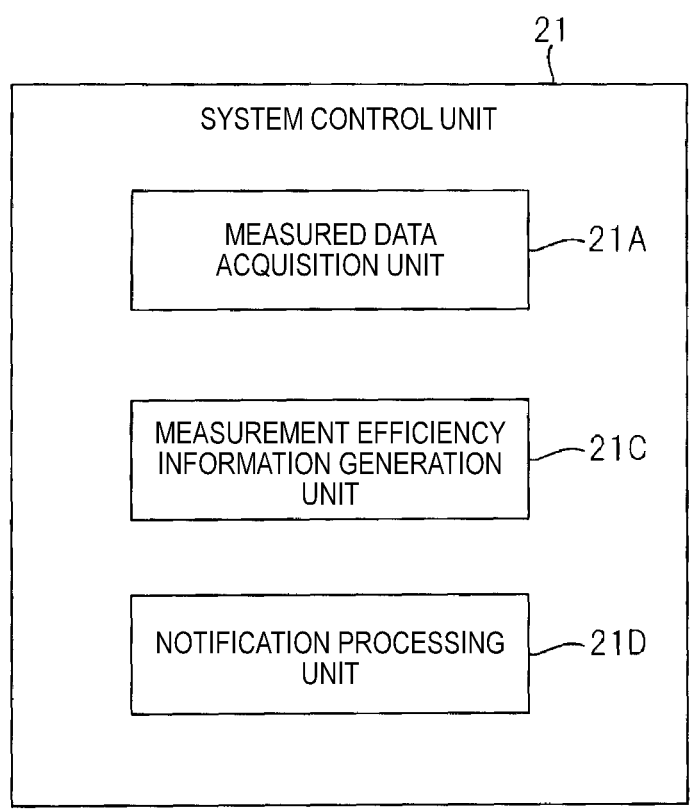
FIG. 14 is a functional block diagram of a system control unit 21 of the electronic device 2 shown in FIG. 13.

FIG. 14 is a functional block diagram of the system control unit 21 of the electronic device 2 shown in FIG. 13.

The system control unit 21 includes a measured data acquisition unit 21A, a measurement efficiency information generation unit 21C, and a notification processing unit 21D.

The measured data acquisition unit 21A, the measurement efficiency information generation unit 21C and the notification processing unit 21D are configured as the programs stored in the ROM are executed by the processor. The programs include a biological information measurement support program. The system control unit 21 configures a biological information measurement support device.

The measured data acquisition unit 21A is configured to acquire the measured data stored in the storage medium 13 from the storage medium 13 of the biological information measurement device 1A and to store the same in the storage medium 23.

The measurement efficiency information generation unit 21C has a function similar to the measurement efficiency information generation unit 11C. When the operation unit 24 of the electronic device 2 is operated to issue a notification instruction of the measurement efficiency information or when the copy of the measured data of the storage medium 13 to the storage medium 23 is completed, for example, the measurement efficiency information generation unit 21C generates the measurement efficiency information, based on the latest measured data stored in the storage medium 23.

The notification processing unit 21D has a function similar to the notification processing unit 11D, and is configured to execute processing of notifying the measurement efficiency information generated by the measurement efficiency information generation unit 21C. The notification processing unit 21D is configured to execute the notification by displaying the information on the display unit 25 or outputting a voice from a speaker (not shown).

Like this, the measurement efficiency information may be generated and notified from the electronic device 2. According to this configuration, it is possible to reduce an amount of the processing in the biological information measurement device 1A and to prolong the battery lifetime of the device. Also, even when the biological information measurement device 1A is not provided with the display unit, the speaker or the like, it is possible to notify the measurement subject of the measurement efficiency information, so that it is also possible to facilitate the miniaturization and cost saving of the biological information measurement device 1A.

Meanwhile, in the diagnosis support system 100, the function of the measurement efficiency information generation unit 21C may be provided to the biological information measurement device 1A. In this case, the system control unit 21 of the electronic device 2 is configured to execute the processing of acquiring the measurement efficiency information from the biological information measurement device 1A and notifying the acquired measurement efficiency information.

Also, in the diagnosis support system 100, the function of the notification processing unit 21D may be provided to the biological information measurement device 1A. In this case, the system control unit 21 of the electronic device 2 is configured to transmit the generated measurement efficiency information to the biological information measurement device 1A. The notification processing unit 21D of the biological information measurement device 1A is configured to acquire the measurement efficiency information and to execute the notification processing.

The notification processing unit 11D and the notification processing unit 21D are basically configured to notify the measurement efficiency information to the measurement subject of the biological information measurement device 1 and the biological information measurement device 1A but may be configured to transmit the measurement efficiency information to a terminal in a hospital that the measurement subject goes to regularly, via the Internet and the like, thereby notifying the measurement efficiency information to a hospital official.

According to the above configuration, the hospital-side can perceive the measurement situations of the patient, and take measures for the patients, such as an advice on an efficient measurement method.

The diverse programs are stored in a non-transitory storage medium from which a computer can read the programs.

The "computer-readable storage medium" includes an optical medium such as a CD-ROM (Compact Disc-ROM), a magnetic recording medium such as a memory card, and the like, for example. Also, the program may be provided by a downloading through a network.

The disclosed embodiments are exemplary in every respect and should not be construed as being limited. The scope of the present invention is defined in the claims, not in the above description, and includes all changes within the meaning and scope equivalent to the claims.

As described above, the specification discloses following items.

A disclosed biological information measurement support device includes a notification processing unit configured to execute processing of acquiring measurement efficiency information and notifying the measurement efficiency information, the measurement efficiency information being generated by a measurement efficiency information generation unit configured to generate the measurement efficiency information based on biological information calculation result information and pulse wave detection result information of a storage medium in which, as information indicative of a calculation result of biological information made by a biological information calculation unit configured to calculate the biological information based on a pulse wave detected from a living body, the biological information calculation result information including at least the biological information calculated based on the pulse wave and the pulse wave detection result information indicative of a result of pulse wave detection processing executed to calculate the biological information to be included in the biological information calculation result information are stored, the measurement efficiency information being indicative of a measurement efficiency of the biological information to be included in the biological information calculation result information.

In the disclosed biological information measurement support device, the pulse wave detection result information includes information of a pulse wave detection time period in which the pulse wave detection processing has been executed, and the biological information calculation result information includes the biological information calculated based on the pulse wave and information of detection time of the pulse wave.

In the disclosed biological information measurement support device, the measurement efficiency information generation unit is configured to generate, as the measurement efficiency information, information indicative of a distribution of time periods, in which pulse waves becoming a calculation source of the biological information of which reliability included in the biological information calculation result information is equal to or higher than a threshold value have been detected, in the pulse wave detection time period.

In the disclosed biological information measurement support device, the measurement efficiency information generation unit is configured to generate, as the measurement efficiency information, information indicative of a relation of a length of a first cumulative time period of time periods, in which pulse waves becoming a calculation source of the biological information of which reliability included in the biological information calculation result information is equal to or higher than a threshold value have been detected, to a length of the pulse wave detection time period or information indicative of a relation of a length of a time period other than the first cumulative time period to a length of the pulse wave detection time period.

In the disclosed biological information measurement support device, the measurement efficiency information generation unit is configured to generate, as the measurement efficiency information, information indicative of a relation of a length of a first cumulative time period, in which pulse waves becoming a calculation source of the biological information of which reliability included in the biological information calculation result information in each divided time period of the pulse wave detection time period is equal to or higher than a threshold value have been detected, to a length of each divided time period or information indicative of a relation of a length of a time period other than the first cumulative time period to a length of each divided time period.

In the disclosed biological information measurement support device, the pulse wave detection result information includes information of all the pulse waves obtained by the pulse wave detection processing or information of a number of all the pulse waves.

In the disclosed biological information measurement support device, the measurement efficiency information generation unit is configured to generate, as the measurement efficiency information, information indicative of a relation of a first number of the biological information of which reliability included in the biological information calculation result information is equal to or higher than a threshold value to a number of all the pulse waves or information indicative of a relation of a number, which is obtained by subtracting the first number from the number of all the pulse waves, to the number of all the pulse waves.

In the disclosed biological information measurement support device, the pulse wave detection result information further includes information of a pulse wave detection time period in which the pulse wave detection processing has been executed, the biological information calculation result information includes the biological information calculated based on the pulse wave and information of detection time of the pulse wave, and the measurement efficiency information generation unit is configured to generate, as the measurement efficiency information, information indicative of a relation of a second number of the biological information of which reliability calculated based on pulse waves detected in each divided time period of the pulse wave detection time period is equal to or higher than a threshold value to a first number of the pulse waves detected in each divided time period or information indicative of a relation of a number, which is obtained by subtracting the second number from the first number, to the first number.

In the disclosed biological information measurement support device, the pulse wave detection result information includes information of some pulse waves of a plurality of pulse waves obtained by the pulse wave detection processing and information of a pulse wave detection time period in which the pulse wave detection processing has been executed.

In the disclosed biological information measurement support device, the measurement efficiency information generation unit is configured to estimate a total number of pulse waves detected during the pulse wave detection time period, based on the information of some pulse waves and the information of the pulse wave detection time period, and to generate, as the measurement efficiency information, information indicative of a relation of a first number of the biological information of which reliability included in the biological information calculation result information is equal to or higher than a threshold value to the estimated total number of pulse waves or information indicative of a relation of a number, which is obtained by subtracting the first number from the total number, to the total number.

In the disclosed biological information measurement support device, the biological information calculation result information includes the biological information calculated based on the pulse wave and information of detection time of the pulse wave, and the measurement efficiency information generation unit is configured to estimate a second number of pulse waves detected in each divided time period of the pulse wave detection time period, based on a total number of the pulse waves, and to generate, as the measurement efficiency information, information indicative of a relation of a third number of biological information, which is calculated based on the pulse waves detected in each divided time period, of the biological information of which reliability included in the biological information calculation result information is equal to or higher than a threshold value to the second number or information indicative of a relation of a number, which is obtained by subtracting the third number from the second number, to the second number.

In the disclosed biological information measurement support device, the biological information calculation result information further includes information indicating that the biological information of which the reliability is equal to or higher than the threshold value could not be calculated, and information indicative of a cause due to which the biological information could not be calculated, and the notification processing unit is configured to notify the information indicative of the cause, together with the measurement efficiency information.

In the disclosed biological information measurement support device, the biological information is blood pressure information.

The disclosed biological information measurement support device further includes the measurement efficiency information generation unit.

In the disclosed biological information measurement support device, when a measurement ending instruction of the biological information is issued to a biological information measurement device including a pulse wave detection unit configured to detect the pulse wave, the biological information calculation unit and a storage control unit configured to store the biological information calculation result information and the pulse wave detection result information in the storage medium, the notification processing unit notifies the measurement efficiency information if a remaining battery level of the biological information measurement device is equal to or less than a remaining level threshold value necessary to perform a measurement operation of the biological information or if a notification instruction of the measurement efficiency information is issued.

A disclosed biological information measurement device includes a pulse wave detection unit configured to detect a pulse wave from a living body, a biological information calculation unit configured to calculate biological information based on the pulse wave detected by the pulse wave detection unit and to store, as information indicative of a calculation result of the biological information, biological information calculation result information including at least the biological information in a storage medium, a storage control unit configured to store, in the storage medium, pulse wave detection result information indicative of a result of pulse wave detection processing executed by the pulse wave detection unit so as to calculate the biological information to be included in the biological information calculation result information, and the biological information measurement support device.

In the disclosed biological information measurement device, the measurement efficiency information generation unit generates the measurement efficiency information when a measurement ending instruction of the biological information or a notification instruction of the measurement efficiency information is issued. When the measurement ending instruction or the notification instruction is issued, the measurement efficiency information generation unit excludes biological information, which is calculated up to a point of time before a predetermined time period from a point of time at which the measurement ending instruction or the notification instruction is issued or after a measurement subject wearing the biological information measurement device wakes up until a point of time at which the measurement ending instruction or the notification instruction is issued and is stored in the storage medium, from the biological information that is to be used for generation of the measurement efficiency information.

In the disclosed biological information measurement device, the measurement efficiency information generation unit is configured to exclude biological information, which is calculated up to a point of time after a predetermined time period elapses from issuance of a measurement start instruction of the biological information and is stored in the storage medium, from the biological information that is to be used for generation of the measurement efficiency information.

The disclosed biological information measurement device further includes a body motion detection unit configured to detect body motion of the measurement subject, and the measurement efficiency information generation unit is configured to exclude biological information, which is calculated for a time period after a measurement start instruction of the biological information is issued until a change amount in the body motion of the measurement subject enters a predetermined range and is stored in the storage medium, from the biological information that is to be used for generation of the measurement efficiency information.

A disclosed biological information measurement support method includes a step of acquiring measurement efficiency information from a measurement efficiency information generation unit and a step of executing processing of notifying the measurement efficiency information, the measurement efficiency information generation unit being configured to generate the measurement efficiency information based on biological information calculation result information and pulse wave detection result information of a storage medium in which, as information indicative of a calculation result of biological information made by a biological information calculation unit configured to calculate the biological information based on pulse waves detected from a living body, the biological information calculation result information including at least the biological information calculated based on the pulse waves and the pulse wave detection result information indicative of a result of pulse wave detection processing executed to calculate the biological information to be included in the biological information calculation result information are stored, the measurement efficiency information being indicative of a measurement efficiency of the biological information to be included in the biological information calculation result information.

A disclosed non-transitory computer-readable storage medium, which stores a biological information measurement support program is configured to enable a computer to execute a step of acquiring measurement efficiency information from a measurement efficiency information generation unit and a step of executing processing of notifying the measurement efficiency information, the measurement efficiency information generation unit being configured to generate the measurement efficiency information based on biological information calculation result information and pulse wave detection result information of a storage medium in which, as information indicative of a calculation result of biological information made by a biological information calculation unit configured to calculate the biological information based on pulse waves detected from a living body, the biological information calculation result information including at least the biological information calculated based on the pulse waves and the pulse wave detection result information indicative of a result of pulse wave detection processing executed to calculate the biological information to be included in the biological information calculation result information are stored, the measurement efficiency information being indicative of a measurement efficiency of the biological information to be included in the biological information calculation result information.

According to the present invention, it is possible to provide the biological information measurement support device, the biological information measurement device, the biological information measurement support method and the biological information measurement support program capable of supporting the efficient measurement of the biological information.

The present invention can be conveniently and effectively used for a blood pressure meter, particularly.

Although the present invention has been described with reference to the specific embodiment, the present invention is not limited to the embodiments and can be diversely changed without departing from the disclosed technical spirit of the present invention.

What is claimed is:

1. A biological information measurement support device comprising:
   a notification processing unit configured to execute processing of acquiring measurement efficiency information and notifying the measurement efficiency information, wherein
   the measurement efficiency information is generated by a measurement efficiency information generation unit configured to generate the measurement efficiency information based on biological information calculation result information and pulse wave detection result information which are stored in a storage medium,
   the biological information calculation result information is indicative of a calculation result of biological information made by a biological information calculation unit configured to calculate the biological information based on a pulse wave detected from a living body,
   the biological information calculation result information includes at least the biological information calculated based on the pulse wave,
   the pulse wave detection result information is indicative of a result of pulse wave detection processing executed to calculate the biological information to be included in the biological information calculation result information,
   the measurement efficiency information is indicative of a measurement efficiency of the biological information to be included in the biological information calculation result information, and
   the measurement efficiency is determined by whether or not the pulse wave satisfies a predetermined condition, which is indicated by a measurement flag.

2. The biological information measurement support device according to claim 1,
   wherein the pulse wave detection result information includes information of a pulse wave detection time period in which the pulse wave detection processing has been executed, and
   wherein the biological information calculation result information includes the biological information calculated based on the pulse wave and information of detection time of the pulse wave.

3. The biological information measurement support device according to claim 2,
   wherein the measurement efficiency information generation unit is configured to generate, as the measurement efficiency information, information indicative of a distribution of time periods, in which pulse waves becoming a calculation source of the biological information of which reliability included in the biological information calculation result information is equal to or higher than a threshold value have been detected, in the pulse wave detection time period.

4. The biological information measurement support device according to claim 2,
   wherein the measurement efficiency information generation unit is configured to generate, as the measurement efficiency information, information indicative of a relation of a length of a first cumulative time period of time periods, in which pulse waves becoming a calculation source of the biological information of which reliability included in the biological information calculation result information is equal to or higher than a threshold value have been detected, to a length of the pulse wave detection time period or information indicative of a relation of a length of a time period other than the first cumulative time period to a length of the pulse wave detection time period.

5. The biological information measurement support device according to claim 2,
   wherein the measurement efficiency information generation unit is configured to generate, as the measurement efficiency information, information indicative of a relation of a length of a first cumulative time period, in which pulse waves becoming a calculation source of the biological information of which reliability included in the biological information calculation result information in each divided time period of the pulse wave detection time period is equal to or higher than a threshold value have been detected, to a length of each divided time period or information indicative of a relation of a length of a time period other than the first cumulative time period to a length of each divided time period.

6. The biological information measurement support device according to claim 1,
   wherein the pulse wave detection result information includes information of all the pulse waves obtained by the pulse wave detection processing or information of a number of all the pulse waves.

7. The biological information measurement support device according to claim 6,
   wherein the measurement efficiency information generation unit is configured to generate, as the measurement efficiency information, information indicative of a relation of a first number of the biological information of which reliability included in the biological information calculation result information is equal to or higher than a threshold value to a number of all the pulse waves or information indicative of a relation of a number, which is obtained by subtracting the first number from the number of all the pulse waves, to the number of all the pulse waves.

8. The biological information measurement support device according to claim 6,
wherein the pulse wave detection result information further comprises information of a pulse wave detection time period in which the pulse wave detection processing has been executed,
wherein the biological information calculation result information includes the biological information calculated based on the pulse wave and information of detection time of the pulse wave, and
wherein the measurement efficiency information generation unit is configured to generate, as the measurement efficiency information, information indicative of a relation of a second number of the biological information of which reliability calculated based on pulse waves detected in each divided time period of the pulse wave detection time period is equal to or higher than a threshold value to a first number of the pulse waves detected in each divided time period or information indicative of a relation of a number, which is obtained by subtracting the second number from the first number, to the first number.

9. The biological information measurement support device according to claim 1,
wherein the pulse wave detection result information includes information of some pulse waves of a plurality of pulse waves obtained by the pulse wave detection processing and information of a pulse wave detection time period in which the pulse wave detection processing has been executed.

10. The biological information measurement support device according to claim 9,
wherein the measurement efficiency information generation unit is configured to estimate a total number of pulse waves detected during the pulse wave detection time period, based on the information of some pulse waves and the information of the pulse wave detection time period, and
wherein the measurement efficiency information generation unit is configured to generate, as the measurement efficiency information, information indicative of a relation of a first number of the biological information of which reliability included in the biological information calculation result information is equal to or higher than a threshold value to the estimated total number of pulse waves or information indicative of a relation of a number, which is obtained by subtracting the first number from the total number, to the total number.

11. The biological information measurement support device according to claim 10,
wherein the biological information calculation result information includes the biological information calculated based on the pulse wave and information of detection time of the pulse wave,
wherein the measurement efficiency information generation unit is configured to estimate a second number of pulse waves detected in each divided time period of the pulse wave detection time period, based on a total number of the pulse waves, and wherein the measurement efficiency information generation unit is configured to generate, as the measurement efficiency information, information indicative of a relation of a third number of biological information, which is calculated based on the pulse waves detected in each divided time period, of the biological information of which reliability included in the biological information calculation result information is equal to or higher than a threshold value to the second number or information indicative of a relation of a number, which is obtained by subtracting the third number from the second number, to the second number.

12. The biological information measurement support device according to claim 1,
wherein the biological information calculation result information further includes information indicating that the biological information of which the reliability is equal to or higher than the threshold value could not be calculated, and information indicative of a cause due to which the biological information could not be calculated, and
wherein the notification processing unit is configured to notify the information indicative of the cause, together with the measurement efficiency information.

13. The biological information measurement support device according to claim 1,
wherein the biological information is blood pressure information.

14. The biological information measurement support device according to claim 1, further comprising the measurement efficiency information generation unit.

15. The biological information measurement support device according to claim 1,
wherein when a measurement ending instruction of the biological information is issued to a biological information measurement device comprising a pulse wave detection unit configured to detect the pulse wave, the biological information calculation unit and a storage control unit configured to store the biological information calculation result information and the pulse wave detection result information in the storage medium, the notification processing unit notifies the measurement efficiency information if a remaining battery level of the biological information measurement device is equal to or less than a remaining level threshold value necessary to perform a measurement operation of the biological information or if a notification instruction of the measurement efficiency information is issued.

16. A biological information measurement device comprising:
a pulse wave detection unit configured to detect a pulse wave from a living body;
a biological information calculation unit configured to calculate biological information based on the pulse wave detected by the pulse wave detection unit and to store, as information indicative of a calculation result of the biological information, biological information calculation result information comprising at least the biological information in a storage medium;
a storage control unit configured to store, in the storage medium, pulse wave detection result information indicative of a result of pulse wave detection processing executed by the pulse wave detection unit to calculate the biological information to be included in the biological information calculation result information; and the biological information measurement support device according to claim 1.

17. The biological information measurement device according to claim 16,
wherein the measurement efficiency information generation unit generates the measurement efficiency information when a measurement ending instruction of the biological information or a notification instruction of the measurement efficiency information is issued, and
wherein when the measurement ending instruction or the notification instruction is issued, the measurement efficiency information generation unit excludes biological information, which is calculated up to a point of time before a predetermined time period from a point of time at which the measurement ending instruction or the notification instruction is issued or after a measurement subject wearing the biological information measurement device wakes up until a point of time at which the measurement ending instruction or the notification instruction is issued and is stored in the storage medium, from the biological information that is to be used for generation of the measurement efficiency information.

18. The biological information measurement device according to claim 16,
wherein the measurement efficiency information generation unit is configured to exclude biological information, which is calculated up to a point of time after a predetermined time period elapses from issuance of a measurement start instruction of the biological information and is stored in the storage medium, from the biological information that is to be used for generation of the measurement efficiency information.

19. The biological information measurement device according to claim 16, further comprising a body motion detection unit configured to detect body motion of the measurement subject,
wherein the measurement efficiency information generation unit is configured to exclude biological information, which is calculated for a time period after a measurement start instruction of the biological information is issued until a change amount in the body motion of the measurement subject enters a predetermined range and is stored in the storage medium, from the biological information that is to be used for generation of the measurement efficiency information.

20. A biological information measurement support method comprising:
a step of acquiring measurement efficiency information from a measurement efficiency information generation unit, the measurement efficiency information generation unit being configured to generate the measurement efficiency information based on biological information calculation result information and pulse wave detection result information of a storage medium in which, as information indicative of a calculation result of biological information made by a biological information calculation unit configured to calculate the biological information based on pulse waves detected from a living body, the biological information calculation result information including at least the biological information calculated based on the pulse waves and the pulse wave detection result information indicative of a result of pulse wave detection processing executed to calculate the biological information to be included in the biological information calculation result information are stored, the measurement efficiency information being indicative of a measurement efficiency of the biological information to be included in the biological information calculation result information, and the measurement efficiency being determined by whether or not the pulse waves satisfy a predetermined condition, which is indicated by a measurement flag, and
a step of executing processing of notifying the measurement efficiency information.

21. A non-transitory computer-readable storage medium, which stores a biological information measurement support program configured to enable a computer to execute:
a step of acquiring measurement efficiency information from a measurement efficiency information generation unit, the measurement efficiency information generation unit being configured to generate the measurement efficiency information based on biological information calculation result information and pulse wave detection result information of a storage medium in which, as information indicative of a calculation result of biological information made by a biological information calculation unit configured to calculate the biological information based on pulse waves detected from a living body, the biological information calculation result information including at least the biological information calculated based on the pulse waves and the pulse wave detection result information indicative of a result of pulse wave detection processing executed to calculate the biological information to be included in the biological information calculation result information are stored, the measurement efficiency information being indicative of a measurement efficiency of the biological information to be included in the biological information calculation result information, and the measurement efficiency being determined by whether or not the pulse waves satisfy a predetermined condition, which is indicated by a measurement flag, and
a step of executing processing of notifying the measurement efficiency information.

* * * * *